United States Patent
Seifert et al.

(10) Patent No.: US 11,865,061 B2
(45) Date of Patent: Jan. 9, 2024

(54) ORTHOPAEDIC TECHNICAL DEVICE CONTROLLED BY AN ACTUATOR AND METHOD FOR CONTROLLING SAME

(71) Applicant: Otto Bock Healthcare Products GmbH, Vienna (AT)

(72) Inventors: Dirk Seifert, Vienna (AT); Roland Auberger, Vienna (AT); Christian Breuer-Ruesch, Vienna (AT); Alexander Noah Spring, Ottawa (CA); Marco Volkmar, Duderstadt (DE)

(73) Assignee: OTTO BOCK HEALTHCARE PRODUCTS GMBH, Vienna (AT)

( * ) Notice: Subject to any disclaimer, the term of this patent is extended or adjusted under 35 U.S.C. 154(b) by 126 days.

(21) Appl. No.: 15/733,314

(22) PCT Filed: Dec. 19, 2018

(86) PCT No.: PCT/EP2018/085781
§ 371 (c)(1),
(2) Date: Jun. 24, 2020

(87) PCT Pub. No.: WO2019/129563
PCT Pub. Date: Jul. 4, 2019

(65) Prior Publication Data
US 2021/0113415 A1    Apr. 22, 2021

(30) Foreign Application Priority Data
Dec. 27, 2017 (DE) ...................... 10 2017 131 319.2

(51) Int. Cl.
| | |
|---|---|
| A61H 3/00 | (2006.01) |
| A61F 2/64 | (2006.01) |
| A61F 2/72 | (2006.01) |
| A61H 1/02 | (2006.01) |
| A61F 2/50 | (2006.01) |
| A61F 2/76 | (2006.01) |
| A61F 2/74 | (2006.01) |

(52) U.S. Cl.
CPC .................. *A61H 3/00* (2013.01); *A61F 2/64* (2013.01); *A61F 2/72* (2013.01); *A61H 1/024* (2013.01);
(Continued)

(58) Field of Classification Search
CPC ............................................ A61H 2201/1246
See application file for complete search history.

(56) References Cited

U.S. PATENT DOCUMENTS 2,530,286 A * 11/1950 Catranis .................... A61F 2/64
188/300
2,605,474 A *  8/1952 Oliver ....................... A61F 2/68
623/44

(Continued)

FOREIGN PATENT DOCUMENTS

| | | | |
|---|---|---|---|
| DE | 10 2014 009 028 A1 | 2/2015 | |
| DE | 10 2013 013 810 B3 | 12/2015 | |

(Continued)

OTHER PUBLICATIONS

International Search Report for International Application No. PCT/EP2018/085781, dated Apr. 9, 2019, 6 pages.

*Primary Examiner* — Jacqueline Woznicki
(74) *Attorney, Agent, or Firm* — HOLLAND & HART LLP

(57) ABSTRACT

An orthopedic technical device having a top part and a bottom part, which are connected to each other by at least one joint device so as to be pivotable about a joint axis, and at least one attachment device with which the orthopedic technical device can be fixed to a limb. The orthopedic technical device also has an actuator, which is fixed to attachment points on the top part and the bottom part and influences a pivoting of the top part relative to the bottom part, wherein the orientation of the bottom part can be (Continued)

adjusted relative to the limb which is fixable to the upper part.

18 Claims, 13 Drawing Sheets

(52) U.S. Cl.
CPC .............. *A61H 1/0277* (2013.01); *A61F 2/74* (2021.08); *A61F 2/748* (2021.08); *A61F 2002/502* (2013.01); *A61F 2002/5018* (2013.01); *A61F 2002/7625* (2013.01); *A61F 2002/7635* (2013.01); *A61H 2201/0165* (2013.01); *A61H 2201/0173* (2013.01); *A61H 2201/1246* (2013.01); *A61H 2201/1638* (2013.01); *A61H 2201/1642* (2013.01); *A61H 2201/1664* (2013.01); *A61H 2201/1671* (2013.01); *A61H 2201/1676* (2013.01); *A61H 2201/5061* (2013.01); *A61H 2201/5069* (2013.01); *A61H 2205/06* (2013.01); *A61H 2205/102* (2013.01); *A61H 2230/085* (2013.01)

(56) References Cited

U.S. PATENT DOCUMENTS

| 4,872,665 | A | * | 10/1989 | Chareire | ............... | A61F 5/0102 |
| | | | | | | 601/35 |
| 6,666,796 | B1 | * | 12/2003 | MacCready, Jr. | ..... | A61F 5/0102 |
| | | | | | | 135/65 |
| 9,730,824 | B2 | | 8/2017 | Gilbert et al. | | |
| 9,968,468 | B2 | | 5/2018 | Auberger et al. | | |
| 2010/0125229 | A1 | * | 5/2010 | Rudolph | ................. | A61H 3/008 |
| | | | | | | 600/595 |
| 2010/0305716 | A1 | * | 12/2010 | Pusch | ........................ | A61F 2/68 |
| | | | | | | 623/24 |
| 2011/0087339 | A1 | * | 4/2011 | Pusch | ........................ | A61F 2/64 |
| | | | | | | 623/43 |
| 2011/0130846 | A1 | | 6/2011 | Kampas | | |
| 2013/0331744 | A1 | * | 12/2013 | Kamon | ................. | A61H 1/0266 |
| | | | | | | 601/35 |
| 2014/0330393 | A1 | | 11/2014 | Ward et al. | | |
| 2015/0112449 | A1 | * | 4/2015 | Chabloz | .................... | A61F 2/80 |
| | | | | | | 623/33 |
| 2016/0058580 | A1 | * | 3/2016 | Bartlett | .................... | A61F 2/64 |
| | | | | | | 623/46 |
| 2017/0156963 | A1 | | 6/2017 | Tuttemann et al. | | |
| 2018/0256372 | A1 | | 9/2018 | Boiten | | |

FOREIGN PATENT DOCUMENTS

| JP | 2011-510766 | A | 4/2011 |
| WO | 2008103917 | A1 | 8/2008 |
| WO | 2009097841 | A1 | 8/2009 |
| WO | 2009140956 | A2 | 11/2009 |
| WO | 2011123928 | A1 | 10/2011 |
| WO | 2016169855 | A1 | 10/2016 |

* cited by examiner

ORTHOPAEDIC TECHNICAL DEVICE CONTROLLED BY AN ACTUATOR AND METHOD FOR CONTROLLING SAME

CROSS REFERENCE TO RELATED APPLICATIONS

This application is a U.S. National Entry and claims priority to PCT International Patent Application No. PCT/EP2018/085781, filed 19 Dec. 2018, and entitled "ORTHOPAEDIC TECHNICAL DEVICE AND METHOD FOR CONTROLLING SAME", which claims priority to Germany Patent Application No. 10 2017 131 319.2 filed 27 Dec. 2017, the entire disclosures of which are incorporated herein by this reference.

TECHNICAL FIELD

The invention relates to an orthopedic device, in particular an orthosis or exoskeleton, with an upper part and a lower part, which are connected to each other by a joint device so as to be pivotable about a joint axis and have fastening devices with which the orthopedic device, e.g. exoskeleton or orthosis, can be secured to a limb, and with an actuator, which is secured to the upper part and the lower part at fastening points and influences a pivoting of the upper part relative to the lower part. The invention further relates to a method for controlling an orthopedic device, in particular an orthosis or exoskeleton, with an upper part and a lower part, which are connected to each other by a joint device so as to be pivotable about a joint axis and have fastening devices with which the orthopedic device, e.g. exoskeleton or orthosis, can be secured to a limb, and with an actuator, which is secured to the upper part and the lower part at fastening points and influences a pivoting of the upper part relative to the lower part, and with at least one sensor coupled to a controller which activates or deactivates an adjustment device for adjusting an extension stop that limits a maximum joint angle.

Orthoses or exoskeletons, together referred to below as orthoses, are used inter alia to support or maintain the function of a still present extremity or limb. For this purpose, the orthosis is secured to the limb. In the case of an orthosis of the lower extremity, for example an orthosis engaging over the knee joint, upper parts and lower parts or rails are placed on the thigh and on the lower leg and are connected to one another via a joint device, the orthotic knee joint. In the case of an ankle orthosis, the foot is fixed on a foot part which is connected via an orthotic ankle joint to a lower-leg part, which in turn serves as upper part. The same applies to a hip joint orthosis or to an orthosis that bridges more than two natural joints. There are also orthoses for upper extremities, for example an orthosis that bridges the elbow joint. The upper part is in each case regarded as the proximal component of an orthosis and is connected to a distal component as lower part via the joint device. Fastening devices take the form of shells, straps, clasps or other devices that prevent the limb from coming loose from the orthosis.

BACKGROUND

Prostheses serve to replace a lost limb and are often equipped with a prosthetic joint which pivotably connects two prosthesis components to each other. In order to influence the movement of the components relative to each other, use is made of actuators, e.g. dampers, brakes and/or drives, which, either controlled or uncontrolled, influence pivoting movements, in particular damp or support such movements.

In order to influence the movements of the upper part and lower part relative to each other during the pivoting movement, for example in order to assist or impede the pivoting movement, use is made of actuators which are secured to the upper part and the lower part. Movement assistance can be effected by supply of energy from an energy store in an embodiment of the actuator as a drive. The energy store can take the form of spring devices or electrical energy stores for driving a motor or a pump. Purely passive actuators are dampers or brakes which provide an adjustable resistance against the pivoting movement. The damping can be used both in terms of the flexion direction and also the extension direction. Stop elements are present in the respective joint device or in the actuator, such that, when a maximum position of the upper part relative to the lower part is reached, a further movement is avoided and a stop is ensured. The stop elements can be provided both for a flexion direction, in which a joint angle is reduced, and also for the extension direction, in which the joint angle is increased. The maximum extension angle is generally reached when there is an angle of 180° between the longitudinal orientation of the upper part and the lower part. The joint angle correlating to this derives from the position of maximum extension dictated by the anatomical and physiological circumstances of the patient's body. These can also represent an in most cases pathological hyperextension position, as a result of which the joint angle can be over 180°. Hyperextension can occur, for example, in the case of a knee joint in which the angle between the rear aspect of the calf and the rear aspect of the thigh can be greater than 180°. Correspondingly, hyperextension occurs in the case of an elbow joint when there is an angle of less than 180° between the forearm and the triceps side of the upper arm.

WO 2009/097841 A1 discloses an orthopedic knee joint, comprising an upper part, on which upper attachment means are arranged, and a lower part pivotably mounted on the upper part, with attachment means for orthopedic components, and a stop for limiting an extension movement. The stop is configured displaceably and is coupled to an adjustment device, which is coupled in turn to a controller which, in accordance with sensor data, actuates the adjustment device and changes the position of the stop. The orthopedic knee joint can also be designed as an orthotic knee joint. The application concerns adapting the position of the extension stop to different instantaneous or short-term demands during walking and standing. Adaptation to the anatomical conditions presented by the user is not disclosed.

The position of the extension stop of an orthosis has to be adapted to the anatomical and physiological circumstances of the particular user. In addition to static extension stops, which are set once during the adaptation of the orthosis to the patient and are not altered until renewed adjustment by an orthopedic technician, the quality of the setting of the extension stop depends on the level of experience of the orthopedic technician. The setting is made easier in the case of extension stop positions that are adjustable by motor, where the individual positions themselves have to be stored in the control system or be input by the orthopedic technician. Correction of extension stop positions may be necessary, for example, in order to be able to correct manufacturing inaccuracies or to take account of flexion contractures in pathological states. These contractures may change over the course of time, for example as a reaction to therapy. Changes may also occur over the course of a day, caused by the activities of the patient. Therefore, a correction of the extension stop position or of the orientation of the limb on the upper part relative to the lower part may be necessary in order to make changes during daily wear or in order to react to different movement situations.

SUMMARY

The object of the present invention is to make available an orthopedic device and a method for controlling an orthopedic device, which in a simple way improve the wearing comfort for the user of the orthosis and permit adaptation to changing anatomical and physiological circumstances.

According to the invention, this object is achieved by an orthopedic device having the features disclosed herein and by a method having the features of also disclosed herein. Advantageous embodiments and developments of the invention are disclosed in the description and the figures.

In the orthopedic device according to the invention with an upper part and a lower part, which are connected to each other by a joint device so as to be pivotable about a joint axis and have fastening devices with which the orthopedic device can be secured to a limb, and with an actuator, which is secured to the upper part and the lower part at fastening points and influences a pivoting of the upper part relative to the lower part, provision is made that the orientation of the lower part is adjustable relative to the limb that can be secured to the upper part. In addition to a change of the orientation of the upper part relative to the lower part about the pivot axis of the joint device by a change of the end stops of the joint device and therefore the change of the end positions of the upper part and of the lower part relative to each other, it is possible to change the orientation of the limb on or in the upper part or lower part relative to the upper part or lower part. In this way, in an embodiment of the orthopedic device as an orthosis, the maximum attainable extension angle and/or flexion angle of the limb can be repeatedly changed without manipulating the joint device or the actuator. In an embodiment of the orthopedic device as a prosthesis, the orientation of the stump in or on the upper part can be changed or the stump can be used in different orientations in the upper part, e.g. in a prosthesis socket, as a result of which the orientation of the lower part to the stump can be changed and can be fixed in the respective position. Maneuvers carried out on the prosthetic joint are not necessary for this purpose. Alternatively or in addition, the orientation can be changed by changes on or in the actuator, since the maximum attainable angle in the flexion direction and/or extension direction is limited and changed by a change of the maximum range of movement of the actuator in one or other direction. Alternatively or in addition, the orientation of the lower part relative to the upper part can be achieved by adjustable stops or limits on the upper part and/or lower part or the joint device, for example by mechanical stops, hydraulic stops or other setting or adjusting mechanisms.

An adjustable extension stop can be arranged and/or formed on the orthopedic device, and/or an exchangeable or adjustable support for the limb can be arranged thereon. The support can be configured as a padding, insert, cushion or inlay, which is variable in terms of its position and/or its volume, such that a changed orientation of the upper part and/or lower part relative to the limb can be achieved. The support can be arranged on a rail, a shell or a socket and can be displaced relative thereto by adjustment devices. Cushions or pads can be filled or emptied in order to change orientations. Alternatively or in addition, an adjustable flexion stop can be arranged or formed on the orthopedic device in order to achieve a mechanical or electronically controlled limitation of the pivoting of the joint device. In a variant of the invention, the extension stop is formed on or in the actuator, on or in a force-transmitting interface between the actuator and the upper part and/or lower part, and/or on or in the at least one joint device.

In a development of the invention, provision is made that the distance of at least one fastening point from the joint axis is adjustable. Mechanical end stops on the joint device can be provided which, for example, can be changed via screws or different inserts, such that different joint angles between the upper part and the lower part can be set as maximum joint angle. In addition or alternatively, an adjustment of the extension stop is provided within the actuator by electronically controlled opening and closing of hydraulic lines, or else a change in the actuator itself, for example by a change of the length of the housing or else by a lengthening or shortening of a piston rod via a thread adjustment. An electronically controlled adjustment of the extension stop, which is provided as a variant of the invention, requires a powerful control system, which is used in suitably configured orthoses or prostheses. Intervention in the set-up and in the dimensions of an actuator often proves difficult, since no standard actuators, for example standard hydraulic dampers or hydraulic drives, can then be used. Consequently, the change of the distance of at least one of the fastening points of the actuator on the upper part or the lower part relative to the joint axis is a simple way of adapting the orthopedic device and the extension stop attainable with an unchanged actuator. The extension stop is made available within the actuator by limiting for example the displacement path of a hydraulic piston within a cylinder. Alternatively or in addition, the extension stop can be made available within the actuator by limiting or changing the displacement path of a hydraulic piston within the cylinder. The extension stop can likewise be set or adjusted by suitably closing valves and/or blocking hydraulic lines, if the actuator is designed as a hydraulic actuator.

If the fastening point for example on the upper part is shifted farther proximally from the joint axis, a corresponding stop is reached at a smaller joint angle, i.e. before the position of maximum extension is reached. If the fastening point is shifted farther in the direction of the joint axis, the possible joint angle increases, and the extension stop is adjusted in the direction of an increasing extension or a maximum joint angle. The adjustment of the fastening point can take place in various ways, in particular by at least one of the fastening points being mounted displaceably on the respectively associated upper part or lower part or on a force-transmitting interface. In addition to an adjustability provided at just one point, it is also possible for both fastening points to be displaceable, wherein the proximal fastening point is displaceable on the upper part or on a proximal force-transmitting interface or is adjustable relative to the joint axis, and likewise the distal fastening point is formed adjustably on the lower part or a distal force-transmitting interface of the joint device or of a joint module.

In a development of the invention, provision is made that the fastening point is mounted, adjustable by motor, on the upper part or lower part or on a force-transmitting interface, so as to be able to displace the fastening point or the fastening points, preferably steplessly, and thus adjust the extension stop.

The fastening point can be mounted displaceably or movably, e.g. rotatably, on the upper part or lower part or on a force-transmitting interface of the joint device. The displaceability can in particular be rectilinear, for example in a straight guide rail or groove. The guide rail or the guide groove can also have a curved shape or some other shape, such that it can be formed as a slotted guide with a predefined movement path of the fastening point. Moreover, the fastening point can be mounted rotatably on the upper part or lower part, in which case an eccentric bearing changes the distance of the fastening point from the joint axis. The rotatability can be effected in stages or also steplessly. Similarly, in addition to a motor-driven rotation or an adjustment via a motor, the rotation, displacement or adjustment can be carried out by an orthopedic technician.

In a development of the invention, provision is made that the fastening point is arranged or formed on an adapter on which several fastening devices for the actuator and/or the joint device or a joint module are arranged. The adapter can be secured as a separate component on the upper part and/or the lower part or can be part of the upper part and/or lower part, such that, by suitable selection of the fastening device to which the actuator and/or the joint device is secured, the maximum attainable flexion angle and/or extension angle can be determined and adjusted. By the formation or arrangement of several fastening devices on one adapter, it is possible to secure the actuator and/or the joint device at different positions on the adapter. Each position of the fastening device offers another distance and leads to another extension stop upon full utilization of the extension path for the respective actuator. The fastening point can be arranged or formed on an exchangeable adapter, on which one or more fastening devices for the actuator and/or the joint device are arranged or formed. Instead of several fastening devices for the actuator and/or the joint device, it is also possible for just one fastening device to be formed on the adapter for the actuator and/or the joint device, such that for each extension stop a separate adapter has to be arranged on the upper part and/or lower part. This may be advantageous for the compensation of manufacturing tolerances or for adaptations to long-term changes in the anatomical circumstances presented by the patient. Various adapter plates with different fastening devices, for example patterns of holes or threaded inserts for the actuator, can be secured or arranged on the upper part and/or lower part. The joint device can be designed in particular as a joint module, which can be secured detachably to the upper part and the lower part. The modular set-up facilitates assembly and the adaptability to the particular user.

Alternatively, the fastening point or fastening points can be arranged or formed on an exchangeable component, in order to realize different positions of the fastening point or fastening points for the joint device. Devices for fastening the joint device or possibly also the actuator can be arranged at different locations or positions on the exchangeable components, such that, depending on the component used, a different extension stop is set. Each position of the fastening device offers another distance and leads to another extension stop upon full utilization of the extension path of the respective actuator. The fastening point can also be arranged or formed on an exchangeable component on which one or more fastening devices for the joint device or the actuator are formed.

In a development of the invention, provision is made that the upper part and/or the lower part and/or at least one force-transmitting interface of a joint device are variable in length. The upper part and/or the lower part and/or the force-transmitting interface can have a multi-part design, wherein the joint device is formed in a first part of the upper part and/or lower part or the interface, and the fastening point is arranged or formed on a second part. The first part and the second part of the upper part and/or of the lower part or the interface are connected to each other so as to be displaceable, for example via a frame or a rail which is variable in length, such that the fastening point can be shifted away from the joint device or the joint axis in order to adjust the extension stop. In principle, it is also possible that the first part and the second part are of a telescopic design and can be pushed one into the other and locked in the respective position. It is likewise possible that the first part or upper part and the second part or lower part are arranged pivotably on each other, in order in this way to obtain different distances of fastening points relative to the joint axis.

In a development of the invention, provision is made that the actuator has a housing of variable length and/or a piston rod of variable length, in order to set the maximum displacement path of the actuator. The housing can be designed to be variable in length via a thread or a telescopic embodiment of the housing parts. Alternatively or in addition, can via a piston rod of variable length, for example via a screw sleeve, which is designed to be adjustable and lockable by motor or by hand.

In a development of the invention, provision is made that at least one sensor for detecting the force transmitted between the upper part and the lower part or for detecting the transmitted moment is assigned to the upper part, the lower part or the joint device. Similarly, a sensor can be provided for detecting a joint angle, the spatial position of the upper part and/or of the lower part, or, alternatively or in addition, a sensor for detecting biometric signals of a user can be assigned to the orthopedic device, e.g. orthosis. As biometric signals it is possible, for example, to use myoelectric signals of the musculature of the limbs, e.g. of the limb to which an orthosis is secured or which performs compensation movements, so as to detect muscle activities of the patient and to deduce therefrom whether and to what extent a patient or user is able to perform certain movements, which muscles are contracted, and to what extent they are contracted to perform the movement, and to what extent muscle contractions and control devices for an actuator or the extension stop correspond to medical requirements. The biometric signals can also be captured on untreated limbs, in order to be able to draw conclusions for example in the context of the evaluation of compensation movements. On the basis of the sensor signals, or at least taking account of the sensor signals, it is then possible to set the extension stop positions corresponding to the anatomical conditions or requirements.

The orthopedic device is preferably designed as a controllable device and is provided with or coupled to at least one sensor, which is coupled to a controller which activates or deactivates an adjustment device for adjusting an extension stop that limits a maximum joint angle. The extension stop, in accordance with sensor data, is moved from a starting position, in which the upper part is located in a position of flexion relative to the lower part, to an end position, in which the upper part is located, relative to the lower part, in a position different than the starting position. The controller can be designed to detect the sensor data over a period of time and to compare them to a threshold value, wherein an adjustment of the extension stop takes place only when the threshold value is reached over a defined period of time.

In one development, provision is made that the maximum joint angle is adjustable, and, in accordance with the measured joint angle, the extension stop is adjustable as far as the maximum joint angle. The controller can be configured such that, when the extension stop is reached, the moment effective about the joint axis and/or the force effective between the upper part and the lower part is measured, and, if a threshold value is exceeded, the extension stop is moved in the direction of its end position. If the threshold value is not reached, the extension stop is moved in the opposite direction.

The controller can be further configured to detect resistance values of the actuator during the pivoting movement and to correlate them with sensor values concerning the joint angle and the forces and/or moments prevailing between the upper part and the lower part, and, if a force and moment profile deviates from the resistance profile, to perform an automatic adjustment of the extension stop. Preferably, the extension stop is adjustable auto-adaptively.

In the method according to the invention for controlling an orthopedic device with an upper part and a lower part, which are connected to each other by a joint device so as to be pivotable about a joint axis and have fastening devices with which the orthopedic device, e.g. orthosis or prosthesis, can be secured to a limb, and with an actuator, which is secured to the upper part and the lower part at fastening points and influences a pivoting of the upper part relative to the lower part, and with at least one sensor coupled to a controller which activates or deactivates an adjustment device for adjusting an extension stop that limits a maximum joint angle, provision is made that the extension stop, in accordance with sensor data, is moved from a starting position, in which the upper part is located in a position of flexion relative to the lower part, to an end position, in which the upper part is located, relative to the lower part, in a position different than the starting position, in particular a position of extension. In addition to being mechanically limited, the extension stop can also be limited or changed by a change of a hydraulic system, for example by the controlled opening and closing of valves or blocking devices which prevent further movement of a piston inside a cylinder in a predetermined position, but a position that can be changed on the basis of sensor data.

The maximum possible joint angle is therefore not fixed and instead can be adjusted. The starting position initially set is a maximum joint angle which is flexed, i.e. which provides a flexion of for example the orthotic knee joint. The maximum joint angle is below the maximum extension position of 180°, i.e. a perpendicular orientation of the longitudinal extent of the upper part relative to the lower part. In principle, a hyperextension is also possible as the maximum joint angle. In the case of an orthotic knee joint, hyperextension is present when the rear aspect of the lower leg relative to the rear aspect of the thigh is at an angle of more than 180°; hyperextension of the elbow joint is present when the forearm is extended from the biceps side of the upper arm by an angle of over 180° or the forearm encloses on the triceps side of the upper arm an angle of less than 180°. This method takes account, for example, of a change in the physiological circumstances of a patient in the course of wearing the orthosis. Whereas the movement range may be reduced in the mornings on account of a flexion contracture, i.e. the maximum joint angle that the patient can perform with respect to a maximum extension is located in a flexed position, the flexion contracture can decrease by the movement during the day. If the extension stop were to remain static, too great an extension stop would be set in the mornings, and this would lead to the tissue structures of the patient being overstrained. In addition, problems can arise in the control of orthoses, in which the extension stop is used as a trigger signal. If the extension stop were to remain set at the level of the flexion contracture in the mornings, this would indeed provide permanent signal triggering when the extension stop is reached upon each complete movement, but it would reinforce the flexion contracture and in addition would mean a loss of comfort.

However, if an automatic adjustment of the extension stop is made on the basis of sensor data, it is possible, on the one hand, to take account of changes in the range of movement over the course of a day and, on the other hand, to take account of changes or progress in the state of health, in particular if the range of movement increases. Thus, over a long period of observation of sensor values such as joint angle, forces, moments, accelerations, spatial positions or also myoelectrical or other physiological signals, it is possible to determine whether the user has made progress in terms of mobility and the respective range of movement, such that over a longer period of time, for example several months, the maximum extension stop is shifted to the limit at which the anatomically maximum extension is achieved. In addition, information made available by the sensor or the sensors can be stored over a predefined period of time and evaluated, so as to be able to be used for documentation purposes. In this way, for example, therapeutic progress can be documented.

The sensor data can be detected over a period of time and compared with a threshold value, wherein the adjustment of the extension stop takes place only when the threshold value is reached over a defined period of time. Instead of a measurement at just one instant, the sensor or sensors are able to detect a large number of data items or data profiles and compare them with a threshold value, which has to be reached over the specific defined period of time. It is only when a mobility level or extension level is achieved over a certain period of time that an adjustment of the extension stop in the direction of increasing extension is made, so as to prevent a situation where the detected situation to be assessed is a statistical outlier or involves an atypical movement of an incorrect measurement.

The maximum joint angle can be set and is set in such a way that the movement range of the orthosis is within the limits that are medically acceptable and that are within the anatomical capacity of the respective patient. In accordance with the respectively measured joint angle, the extension stop can be adjusted as far as the maximum attainable joint angle or the therapy goal. The respectively measured joint angle is compared with a setpoint value, threshold value or limit value. The setpoint angle, threshold value or limit value can be slowly adapted over a long period of time, for example by continuous averaging of the measured angle. The changing of the extension stop ends when the predefined maximum joint angle is reached as the defined threshold value, in order to prevent hyperextension of the anatomical structures. The extension stop can also be adjusted on the basis of evaluation of the transmitted joint moment or the transmitted forces at a predefined time. For example, it can be determined that, in the case of an orthosis, a defined moment has to be transmitted by the orthosis in the extended position of the knee joint when walking in one plane. If the moment actually transmitted is too low, this is an indication of possible overloading of the anatomical structures, from which it is possible to infer that the extension stop of the orthosis would have to be adjusted in order for the stop to be effected at a lower joint angle. If the transmitted moment is very high, this can be an indication that the orthosis reaches the extension stop too early, the knee joint could therefore go further in extension, with the orthosis blocking the movement too early. A desired extension effect for the patient is thus not achieved, and the movement cannot be executed fully and correctly, as a result of which the orthosis system as a whole would be inadequate. If very high forces or moments are found in the orthosis when the extension stop is reached, this can lead to the shifting of the extension stop in a direction of an increased joint angle.

Alternatively or in addition, in the adjustment of the extension stop, it is ascertained whether and to what extent, in defined movement phases, a threshold value for the moment effective about the joint axis or for the forces effective between the upper part and the lower part is reached or exceeded. For this purpose, when the instantaneous extension stop is reached, the moment effective about the joint axis or the forces effective between the upper part and the lower part are measured and, if a threshold value is exceeded, the extension stop is shifted in the direction of its end position. If the threshold value is not reached, the extension stop can be shifted in the opposite direction, i.e. the maximum attainable joint angle can be reduced, for example in order to ensure that the extension stop is reached in every complete movement, without overstraining or placing a very heavy load on the anatomical structures. The establishment of defined movement phases prevents undesired adjustment in the event of randomly occurring high moments, for example in the event of stumbling.

It is moreover possible that resistance values of the actuator during the pivoting movement are detected and are correlated with sensor values concerning the joint angle and the forces and/or moments prevailing between the upper part and the lower part. The adaption or adjustment of the extension stop thus takes place on the basis of a relationship between joint angles, moments or force profiles and resistance values. Anatomical joints do not generally have a hard extension stop, and instead they show a certain elasticity on account of ligaments, tendons and capsules around the extension stop. In certain movements, for example in swing phase extension or stance phase extension during walking, this elasticity leads to a characteristic angle-moment profile. The extension movement is braked beyond the extent influenced by the aid itself. According to the invention, the angle range and the moments are determined and are compared with a characteristic angle-moment profile. If the characteristic angle-moment profile is not reached, this is an indication that the extension stop has to be adapted. Thus, for example for the knee joint in the swing extension phase during walking, it can be determined whether the joint is braked strongly in an angle range before the end stop, although the orthosis with the actuator offers a constantly low resistance. It is thus possible to estimate where the natural end stop lies. The position of the extension stop can then be adapted automatically, such that this effect occurs shortly before the end stop, in order to achieve a movement profile that is as natural as possible.

The extension stop is preferably adjusted auto-adaptively, i.e. on the basis of measured sensor values and without the intervention of a patient or orthopedic technician based on previously established criteria. For this purpose, the sensors detect information that forms the basis for the assessment of a possible change of the orthosis property, in particular of the extension stop. In addition to measured values detected by sensors, it is also possible to use calculated or estimated parameters and states of the system, i.e. of the orthosis, together with the patient; these can be parameters and states from over a past period of time and also current parameters and states. Besides angles, moments, forces or spatial positions of upper part and lower part or spatial positions of limbs, there is additionally information concerning the duration of wear, the time of day or the profile of the previous adaptation, for example in which periods of time which changes of the extension stop in the direction of an increasing maximum joint angle or a decreasing maximum joint angle had been achieved. To this extent, evaluation of electromyography sensors may be expedient, in order to draw conclusions regarding the activity of the residual musculature and any existing spasticity.

In a control device with a computer unit in which sensor data and other information items are processed and optionally stored, the existing information items are processed, compared with one another and correlations determined, for example the determination of the joint moment from a joint angle and a hydraulic force in the actuator, taking account of the geometric conditions present in the orthosis. These information items are combined into one or more criteria, and in each case the period of observation forming the basis of the assessment can vary depending on the intended use. In addition, different periods of observation can be applied for different information items, for example sensor data of the current gait cycle, and an adaptation of the extension stop over the last hundred or more steps. From this, it is possible to derive criteria such as extreme values, average values, differences, integral standard deviation, or more complex features such as data series, typographies, correlations. The criteria are then assessed or compared with reference values which, among other things, can be based on patient-specific data. The assessment can take place using classification methods such as neural networks, machine learning or pattern recognition. In an assessment device, the characteristic variables determined from the sensor data are used as a basis for deciding whether and to what extent a change of the extension stop is necessary and how great this change should be.

For carrying out the method, the extension stop can be achieved by a displacement of the fastening points or by any other change, e.g. by controlled blocking of hydraulic lines, by changing the position of the piston rod, by setting mechanical end stops, or by other changes to the joint device, the upper part, the lower part and/or the actuator.

BRIEF DESCRIPTION OF THE DRAWINGS

Illustrative embodiments of the invention are explained in more detail below with reference to the accompanying figures, in which.

DETAILED DESCRIPTION

Figure 1:
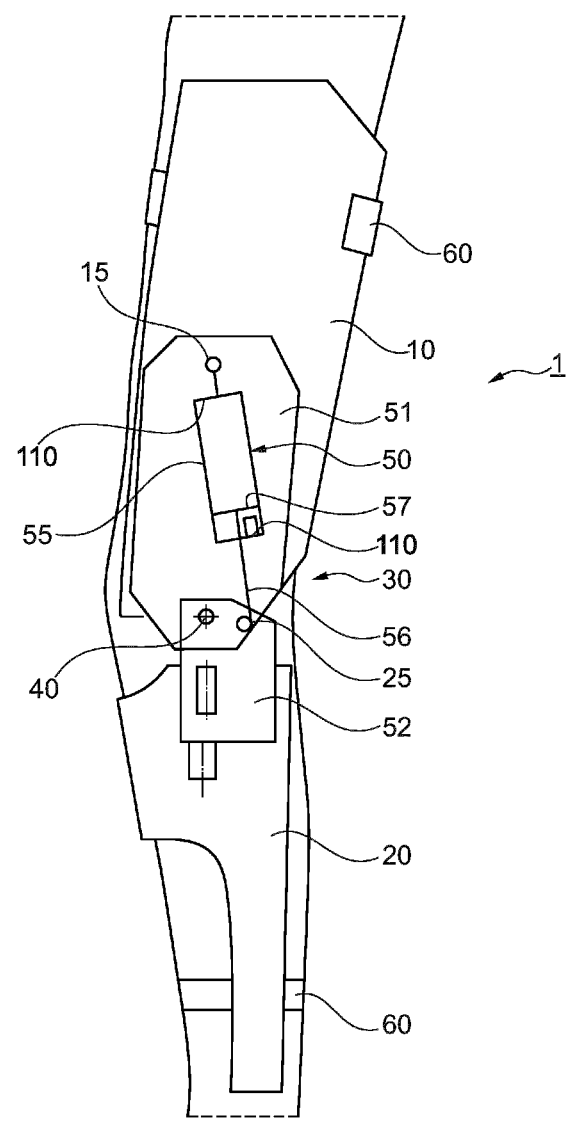
FIG. 1 shows a schematic side view of an orthopedic device.

FIG. 1 is a schematic side view of an orthopedic device 1 in an orthosis engaging over a joint. The orthopedic device 1 has an upper part 10 and a lower part 20, which are connected to each other by a joint device 30 so as to be pivotable about a joint axis 40. A fastening device 60 in the form of a strap is arranged on the upper part 10, which can be designed as a rail or shell, in order to secure the upper part 10 to a limb, in the illustrative embodiment shown to a thigh. Correspondingly, a fastening device 60 is arranged on the lower part 20, in order to couple the lower part 20 to the lower leg and secure it thereon. In an embodiment of the orthopedic device 1 as an arm orthosis, the upper part 10 is secured to an upper arm and the lower part 20 is secured to a forearm. In an embodiment of the orthopedic device as a prosthesis, the upper part 10 is designed as a prosthesis socket in which the limb is secured, for example via a liner and a vacuum source. In the illustrative embodiment shown, the joint device 30 is arranged on one side, preferably laterally on the limb. Alternative embodiments with two joint devices 30, one on the medial side and one on the lateral side of the limb, are likewise provided. Instead of a monocentric embodiment of the joint device 30 with only one joint axis 60, the joint device 30 can also form a multi-axial joint, which is expedient both in the case of prostheses and also in the case of orthoses.

An actuator 50 is secured to the upper part 10 and lower part 20 at fastening points 15, 25. In the illustrative embodiment shown, the securing is effected via force-transmitting interfaces 51, 52, which can be designed as carrier plates, parts of the upper part 10 or lower part 20, adapter plates, frame structures or the like. Provision is also made for the actuator 50 to be fastened directly to the upper part 10 and lower part 20 without interposition of force-transmitting interfaces 51, 52, as will be explained below. The actuator 50 according to FIG. 1 is a hydraulic damper having a housing 55 in which a longitudinally movable hydraulic piston 57 is arranged which, by way of a piston rod 56 protruding from a cylinder inside the housing 55, is coupled to the lower part 20 at the fastening point 25. The housing 55 is secured to the upper part 10, via the force-transmitting interface 51, at a bearing receptacle arranged or formed thereon. The fastening point 25 on the force-transmitting interface 52 for securing to the lower part 20 is located at a distance from the joint axis 40, such that, during a pivoting of the lower part 20 about the joint axis 40, the piston rod 56 together with the piston 57 is moved inside the housing 55 of the actuator 50. In the illustrated position of the orthopedic device 1, i.e. the position of maximum extension, the piston rod 56 is deployed to the maximum extent, the piston 57 bears on an extension stop 110, and further pivoting in the extension direction, i.e. for increasing the joint angle between the upper part 10 and the lower part 20 at the rear face or biceps side of the orthopedic device 1, is not possible. When the lower part 20 is pivoted counter-clockwise about the joint axis 40, a flexion movement is initiated, as a result of which the piston 57 within the housing 55 is displaced upward in the direction of the proximal fastening point 15. The extension stop 110 can be adjustable, for example by its position being changed by screwing into or out of the housing 50. As an alternative to an arrangement of a joint stop, in particular an extension stop 110, in the actuator, a corresponding extension stop 110 can also be arranged in the joint device 30, in order to adjust the orientation of the upper part 10, and of the thigh secured to the upper part 10, relative to the lower leg or the lower part 20. In the context of therapy, it may be necessary to change the extension stop, for example in order to avoid damage to a ligament apparatus or to tissues, or, in the event of therapeutic progress or healing, to be able to permit an increased extension movement.

Figure 2:
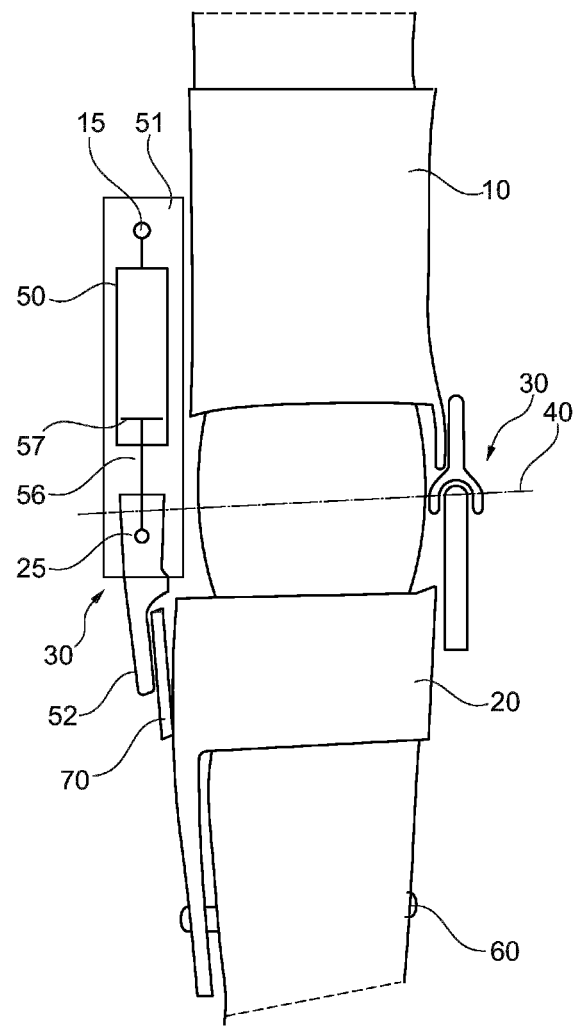
FIG. 2 shows a variant of an orthopedic device in a front view.

FIG. 2 shows a variant of an orthopedic device 1 in the form of an orthosis which engages over a knee joint and has a sleeve-like upper part 10, a lower part 20, and a joint device 30 which is formed by the force-transmitting interfaces 51, 52. The actuator 50 is, for example, arranged laterally on the leg; a second joint device 30 is arranged medially on the upper part 10 and the lower part 20, forming a medial support joint through which the joint axis 40 likewise runs. The upper part 10 and the lower part 20 are arranged on the thigh and lower leg via the fastening devices 60. Alternatively or in addition to an extension stop 110 in the actuator 50 as shown in FIG. 1, an adjustable stop for limiting the flexion angle and/or the extension angle can be arranged on one of the joint devices 30 or on both joint devices 30.

It will also be seen from FIG. 2 that an adapter 70 in the form of an adapter plate is arranged between the distal force-transmitting interface 52 and the lower part 20. By way of the adapter plate, it is possible to provide an angle compensation, for example in order to compensate for manufacturing tolerances or for deviations in the anatomical circumstances of different patients. It is likewise possible to provide a distance compensation via the adapter 70, in order to compensate for medial and/or lateral spaces or gaps between the lower part 20 and the force-transmitting interface 52. This can be achieved, for example, by the adapter or adapter plates 70 having different thicknesses. A fastening point can be arranged or formed on the respective adapter 70. It is likewise possible to provide several bearing receptacles or the like thereon in order, as in the illustrative embodiment shown, to secure the joint device 30, designed as joint module, at different locations or positions thereon, or in order to be able to secure the actuator 50 to the respective upper part 10 or lower part 20 without interposition of force-transmitting interfaces 51, 52. For this purpose, suitable devices are arranged or formed on the adapter 70, in order to secure the respective component thereon. To supplement the arrangement of an adapter 70 on the lower part 20, such an adapter 70, or an adapter 70 of a different kind, can also be arranged on the upper part 10, in order to provide different fastening possibilities for the force-transmitting interface 51 or directly for the actuator 50. An adapter 70 can be arranged both on the upper part 10 and on the lower part 20 or only on one of these components.

Figure 3:
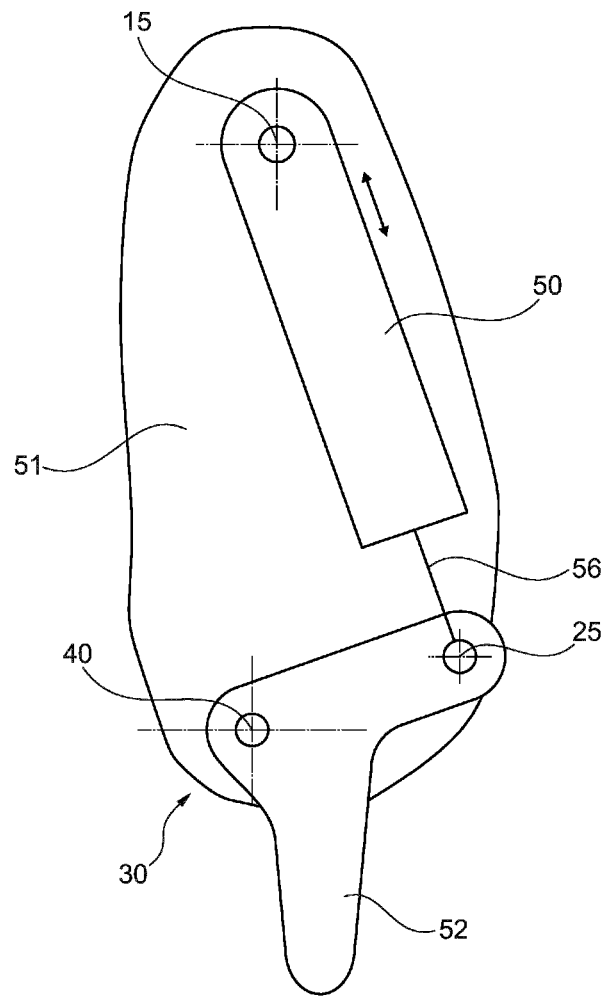
FIG. 3 shows a detailed view of a joint device.

FIG. 3 shows a detailed view of the joint device 30 with the force-transmitting interfaces 51, 52, with the articulated connection about the joint axis 40. The interface 52 for the lower part is designed as an angled bracket, while the interface 51 for the upper part is designed as a plate. In principle, it is also possible to arrange the actuator 50 directly on the upper part and lower part, or else directly on an upper part or lower part and via an interface 51, 52 on the corresponding other orthosis component. To be able to change the maximum extension angle and, if appropriate, the maximum flexion angle between the two interfaces 51, 52 and thus also between the upper part 10 and the lower part 20, the upper fastening point 15 in the illustrative embodiment shown is mounted displaceably on the force-transmitting interface 51, such that the distance between the fastening point 15 and the joint axis 40 is changed. With the same configuration within the actuator 50, i.e. with a mechanical end-stop of the piston within the cylinder, the maximum attainable angle position between the upper part 10 and the lower part 20 thus changes. If, for example, the fastening point 15 is shifted upward, away from the joint axis 40, the lower part flexes and the extension stop, for example when the hydraulic piston abuts the lower distal end of the cylinder, is not reached at a position of maximum extension, but instead at a position of slight flexion. By contrast, if the fastening point 15 is shifted in the direction of the joint axis 40, the lower part 20 can extend further relative to the upper part 10, until a desired or medically acceptable end position of the orthopedic device is reached.

Figure 4:
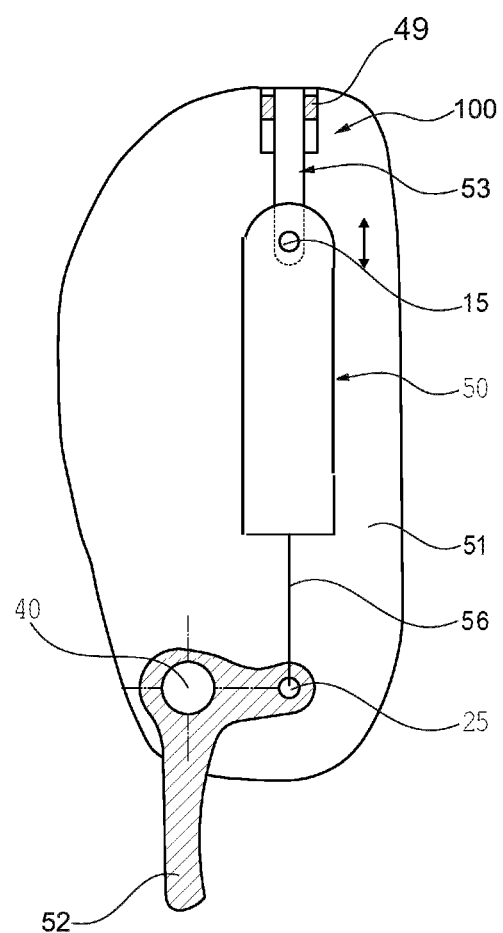
FIG. 4 shows a variant of FIG. 3.

FIG. 4 shows an adjustment variant in which the actuator 50 is secured to an actuator suspension 53. The fastening point 15 is formed between the actuator suspension 53 and the actuator 50. The actuator suspension 53 has, at its upper end, an outer thread which engages with a rotatably mounted, axially secured inner thread 49, which is formed for example in a rotatable sleeve. The sleeve can be rotated manually or by motor in one or other direction and forms an adjustment device 100 via which, depending on the direction of rotation of the sleeve with the inner thread 49, the actuator suspension 53 and thus the entire actuator 50 is shifted upward or downward, i.e. away from the joint axis 40 or in the direction of the joint axis 40. When the actuator 50 together with the actuator suspension 53 is moved downward, the force-transmitting interface 52, which can be secured to the lower part 20, can be pivoted further in the clockwise direction about the joint axis 40, as a result of which the orientation of the upper part relative to the lower part can be changed in terms of the position of maximum extension. When the actuator suspension 53 is shifted upward away from the joint axis 40, the position of maximum extension is already reached when the orthopedic device still adopts a position of flexion, i.e. the lower part 20 adopts, relative to the upper part 10, an angle that is smaller than 180° between the longitudinal extents of the upper part and of the lower part. To adjust the extension stop, there is no need for any change or modification to the actuator 50, which can be designed as a damper or also as a drive; it is possible to use standard actuators 50 which can be secured variably in terms of their position on the upper part 10 or lower part 20 or on the respective force-transmitting interfaces 51, 52.

Figure 5:
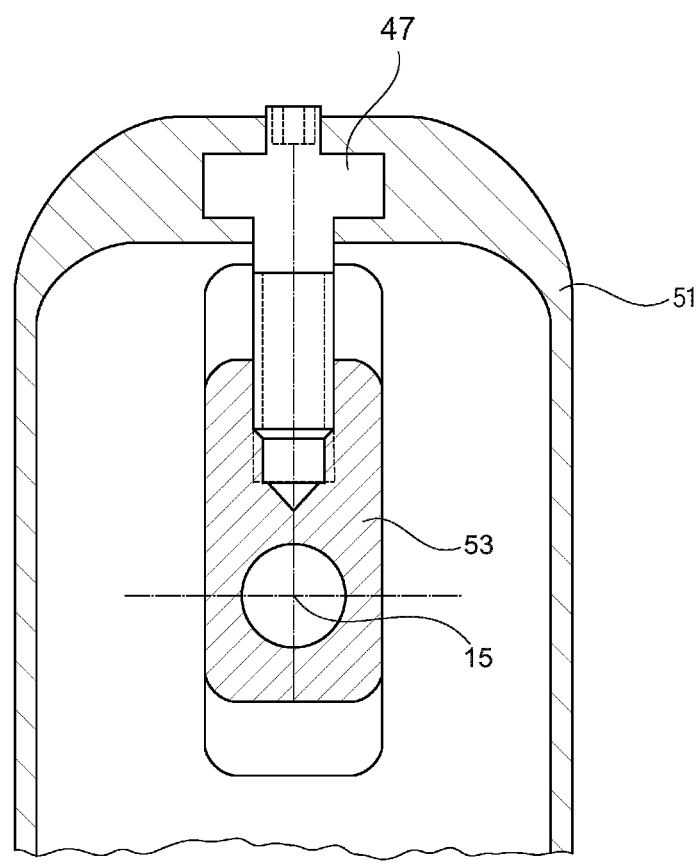
FIG. 5 shows a detailed view of an adjustment device for displaceable adjustment of a fastening point.

FIG. 5 shows a detailed view of a possible adjustment device 100 in which only a part of the force-transmitting interface 51 is shown. The fastening point 15 is arranged on a slide element 53 which is arranged longitudinally displaceably in a recess in the force-transmitting interface 51 or in an upper part 10 or lower part 20. The slide element 53 can be displaced via a set screw 47 which is mounted axially immovably and rotatably on or in the force-transmitting interface 51. Through rotation of the set screw 47 manually or by motor, the fastening point 15 is displaced along the recess in one or other direction, as a result of which the entire actuator 50 is shifted and, therefore, the orientation of a lower part relative to the limb that can be secured to the upper part is adjustable. In particular, the maximum flexion angle and the maximum extension angle between the upper part and the lower part are set.

Figure 6:
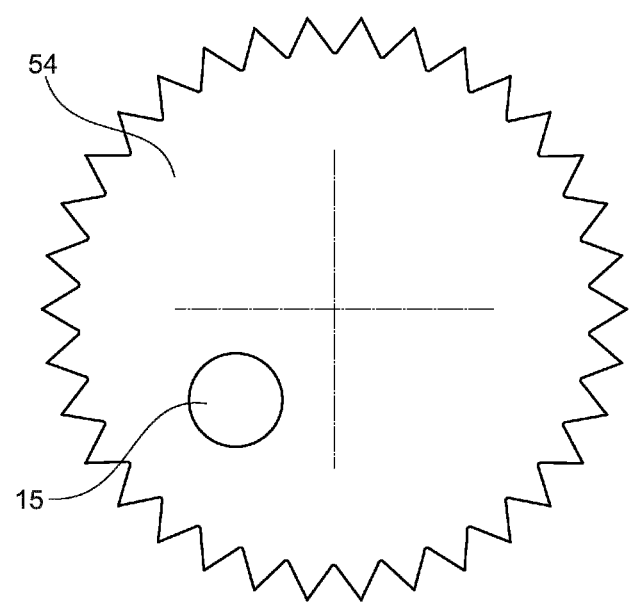
FIG. 6 shows a detailed view of a rotatable fastening point.

An alternative embodiment of an adjustment device 100 is shown in a detailed view in FIG. 6, in which the fastening point 15 or 25, for example a pin, a screw, a threaded insert or a recess, is arranged eccentrically with respect to a rotation axis of a toothed cam 54. A tab or a corresponding toothing system of a locking device can engage in the teeth of the toothed cam 54, in order to secure the toothed cam 54 against unwanted rotation. By virtue of the eccentric arrangement of the fastening point 15 on the toothed cam 54, it is possible, through rotation, to shift the fastening point 15 relative to the joint axis and thereby to adjust the extension stop and likewise the flexion stop of the orthopedic device. The toothed cam 54 can be adjusted manually or by motor; a locking tab for securing against rotation can be spring-loaded in the direction of the outer toothing of the toothed cam 54. The toothing of the cam can also be used as a means of securing against rotation if a corresponding mating contour is located on the force-transmitting interface 51, 52 or on the upper part 10 or the lower part 20. In this case, instead of a toothing, other contours can also conceivably be provided as means of securing against rotation.

Figure 7:
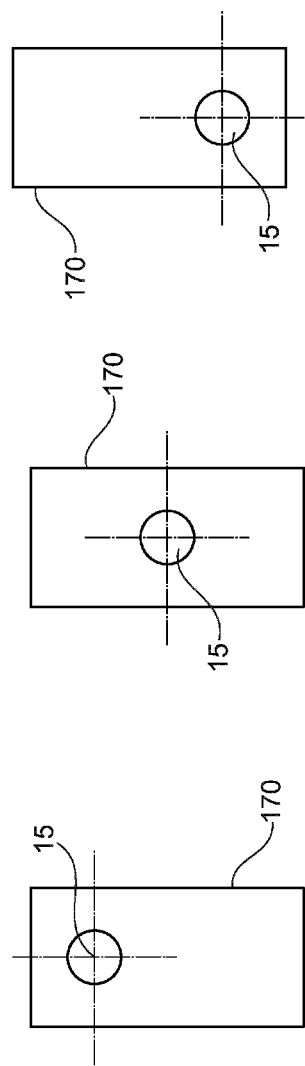
FIG. 7 shows views of different adapters.

FIG. 7 shows a variant of the invention in which, instead of a displaceable bearing according to FIG. 5, an exchangeable component 170 can be placed as an inlay or the like into a recess in the upper part 10, the lower part 20 or one of the two interfaces 51, 52. A fastening point 15 for securing and mounting the actuator 50 is arranged or formed on the respective exchangeable component 170. If the left-hand inlay or exchangeable component 170 is inserted into the recess for example according to FIG. 5, this fastening point 15 is at a maximum distance from the joint axis 40. A limit of the extension movement is reached before the maximum joint angle is reached, which angle is generally reached at a maximum extension of the limb, such that an end-stop is provided at a position of flexion. In the middle view, the exchangeable component 170 is equipped with a centrally arranged fastening point 15, such that its use causes the extension stop to be shifted further forward, and a blocking of the extension movement thus takes place later. The right-hand view shows the exchangeable component 70 with the fastening point 15 at the lowest position, in which the lower part 20 and the upper part 10 are located in a position of maximum extension, when the actuator 50 reaches its end-stop predefined by its design. The displacement of the fastening point 15 can take place both in the proximal-distal direction and in the anterior-posterior direction. Alternatively, any other outer contour of the exchangeable component 170 is conceivable, as long as it secures sufficiently against rotation.

Figure 8:
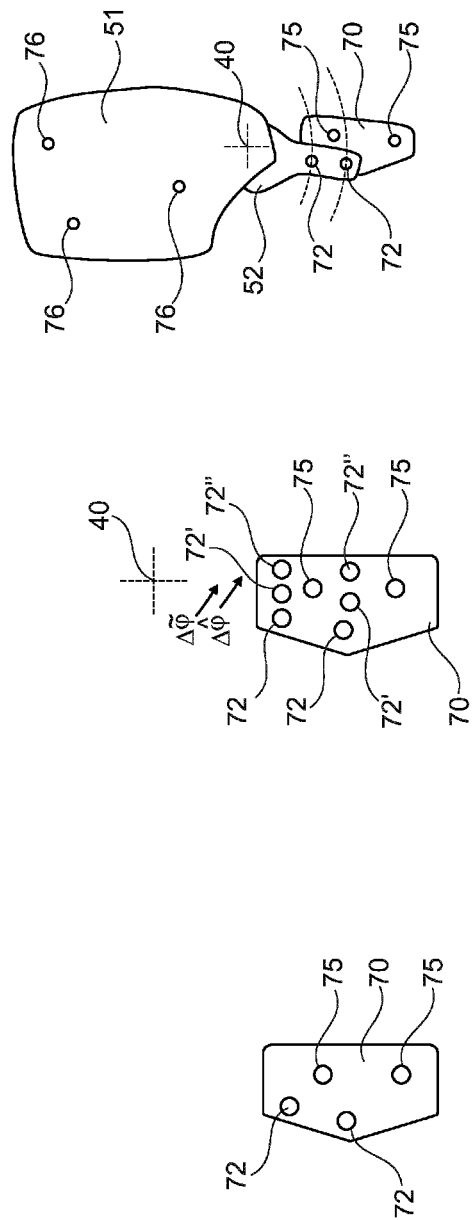
FIG. 8 shows different adapter plates for the orthopedic device.

FIG. 8 shows a further variant of the invention, in which different adapters 70 are shown in the two views on the left. In the view on the right, the adapter 70 is arranged on the force-transmitting interface 52 for securing to the lower part 20 (not shown). On the adapter 70, two fastening devices 75 are arranged or formed to which, for example, the force-transmitting interface 52 or the actuator 50, in particular the piston rod 56, can be secured. The adapter 70 has two recesses or fastening elements 72, with which the adapter 70 can be secured to the force-transmitting interface 52. In the view on the left in FIG. 8, the adapter 70 is shown on its own, from which it can be seen that the two fastening devices 75 are formed at a distance from each other.

Alternatively, at different positions on the upper part 10 or on the force-transmitting interface 51, fastening devices 76 can be arranged with which either the actuator 50 or the joint device 30 can be secured to the upper part 10. By virtue of the large number of fastening devices 76 on the upper part 10 or on the force-transmitting interface 51, different actuator models with different displacement paths and movement ranges can be secured to the orthopedic device.

The middle view in FIG. 8 shows a variant of the adapter 70 in which several fastening elements 72, 72', 72" are arranged on an orbit whose center point coincides with the joint axis 40. It is thereby possible to achieve an angle adjustment through a rotation about the joint axis 40. If, for example, fastening elements 72, 72', 72" are arranged or formed at every 5° on the adapter 70, an offset mounting of the adapter 70 on the lower part 20 or the interface 52 permits a gradation of the extension angle stop of in each case 5°.

Figure 9:
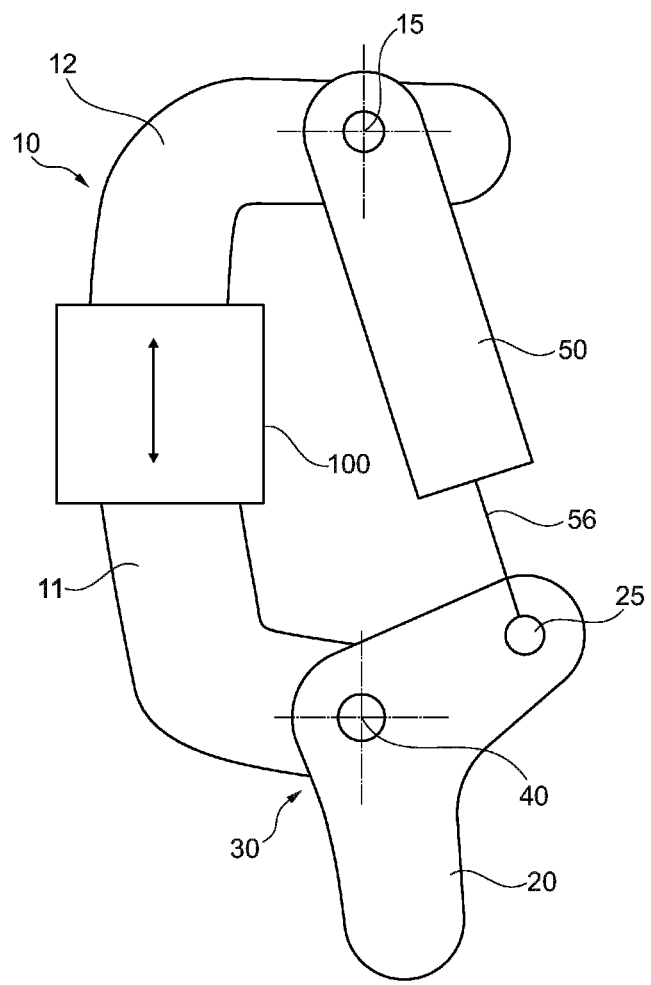
FIG. 9 shows a variant of the invention with an upper part of variable length.

FIG. 9 shows a further variant of the invention, in which the upper part 10 is in two parts. Instead of an upper part 10, a corresponding embodiment can also be realized for a lower part 20 or a force-transmitting interface 51, 52. A first part 11 has a receptacle for the lower part 20 with the joint axis 40 for forming the joint device 30. The second part 12 has the fastening point 15 for the actuator 50. Arranged between the first part 11 and the second part 12 is an adjustment device 100 via which the two parts 11, 12 can be displaced relative to each other. For example, a rectilinear displacement can be effected by the adjustment device 100 via a thread release, a telescopic embodiment or also a rotation or a displacement via a cam, such that the fastening point 15 is shifted away from the joint axis or shifted toward the latter. By means of the corresponding shifting of the fastening point 15 from or to the joint axis 40, as described above, the maximum extension angle between the upper part 10 and the lower part 20 or between the upper part 10 and the force-transmitting interface 52 is changed. Instead of an embodiment of the upper part 10 composed of two parts 11, 12, the force-transmitting interface 51 can also be designed in two parts, and the same applies to the lower part 20 or the second force-transmitting interface 52. Thus, the change in length of the upper part 10, of the lower part 20 or of one of the force-transmitting interfaces 51, 52 brings about a change of the extension stop, and therefore a change of the maximum attainable orientation between the upper part 10 and the lower part 20 and thus between a limb and the lower part 20.

Figure 10:
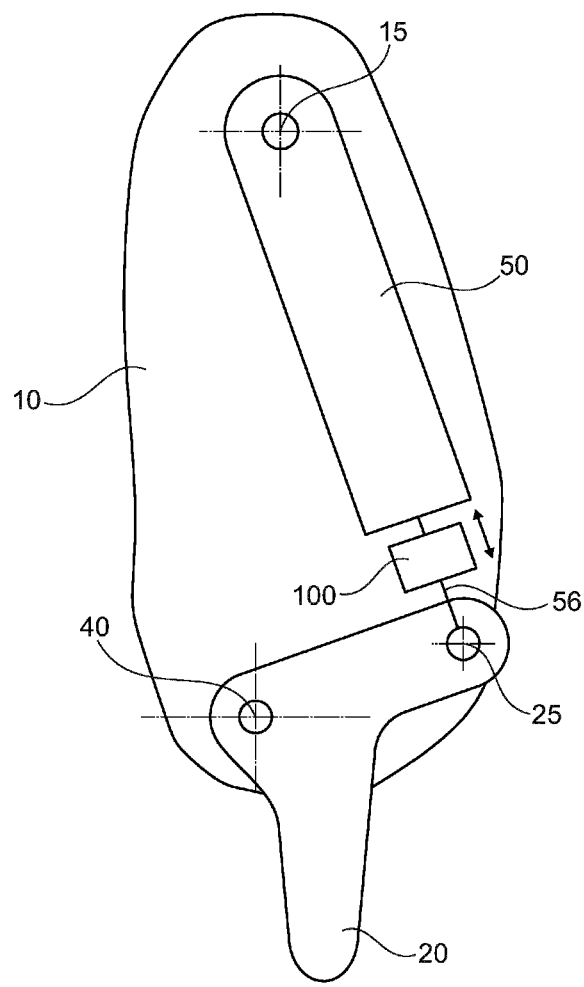
FIG. 10 shows a variant with a piston rod of variable length.

FIG. 10 shows a further variant of the invention. The basic set-up corresponds to that of FIG. 3. Instead of the displacement of the fastening point 15, provision is made in this variant that the piston rod 56 is variable in length. For this purpose, an adjustment device 100 is integrated in the piston rod 56 in order to change the length of the latter. By means of the change in length of the piston rod 56, the maximum extension angle is changed and, consequently, the extension stop is set.

Figure 11:
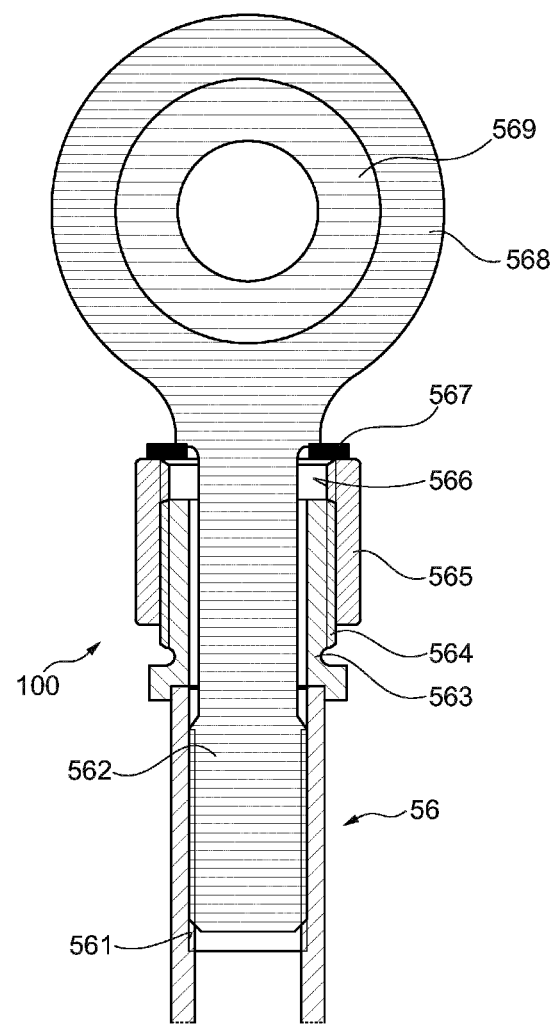
FIG. 11 shows a detailed sectional view of a piston rod of variable length.

FIG. 11 is a sectional view showing an illustrative embodiment of a piston rod 56 of variable length. Inside the piston rod 56 there is an inner thread 561, which interacts with a screw insert 562. The screw insert 562, as a constituent part of the piston rod 56, can be screwed in as far as the end of the inner thread 561, in order to form the minimum length of the piston rod 56 with the screw insert 562, on which a bearing receptacle 568 with a pivot bearing 569 is arranged. The screw insert 562 is unscrewed in order to lengthen the piston rod 56. To secure the adopted position, an adjustment device 100 with two screw sleeves 563, 565 is arranged between the bearing receptacle 568 and the piston rod 56. The lower screw sleeve 563 has an outer thread 564, which interacts with an inner thread 566 of the outer screw sleeve 565. The upper end of the outer screw sleeve 565 is supported on the bearing receptacle 568 via a support disk 567, while the lower end of the inner screw sleeve 563 is supported on the piston rod 56. To secure the adopted position of the screw insert 562 and to build up pre-tensioning in the screw insert 562, the screw sleeves 563, 565 are rotated relative to each other such that the respective ends are braced against the piston rod 56 or the support disk 567, as a result of which a rotation of the screw insert 562 relative to the piston rod 56 is prevented. By virtue of the lengthening of the piston rod or the unscrewing of the screw insert 562, an embodiment according to FIG. 10 permits a pivoting of the lower part 20 in a clockwise direction over a greater angle range, such that the extension stop is shifted further forward, i.e. in the direction of the maximum extension.

Figure 12:
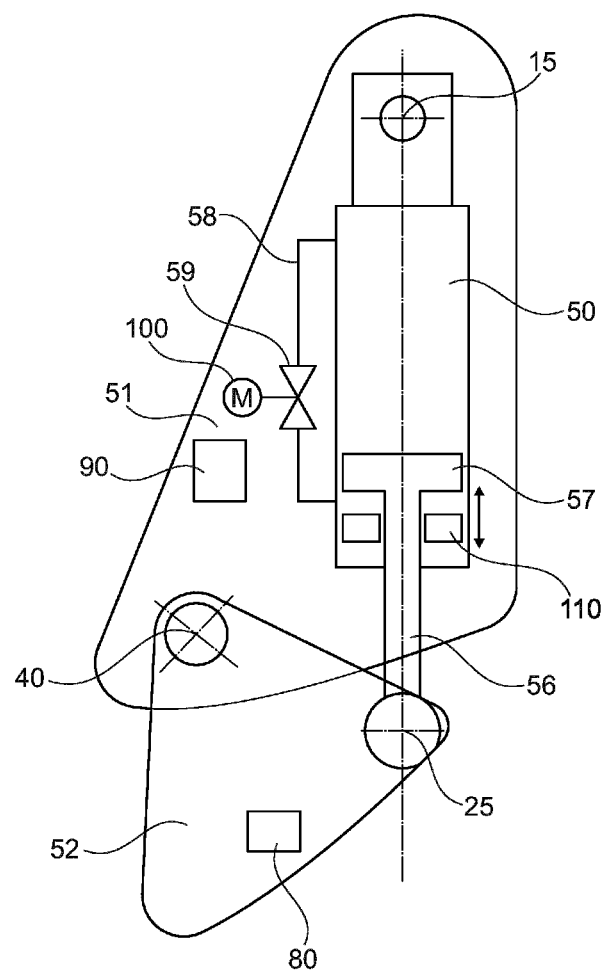
FIG. 12 shows a further variant having different adjustment possibilities.

Variants of the invention are shown in FIG. 12 in which, besides a mechanical extension stop 110 arranged inside the actuator 50 in the cylinder, further possibilities for adjusting the extension stop are shown. As is indicated by the double arrow, the mechanical extension stop 110 can be shifted in the longitudinal extent of the piston rod 56 inside the cylinder in the actuator 50, such that the piston 57 abuts the mechanical extension stop 110. The stop is adjustable. If the extension stop 110 is shifted upward, the extension stop 110 is reached early; the leg or the arm in a position of flexion is prevented from further extension. If the extension stop 110 is shifted further downward in the direction of the lower fastening point 25, the pivoting angle in the extension direction about the joint axis 40 increases. Alternatively, outer thread 564 and inner thread 566 can also be changed around between the two components 563 and 565.

Alternatively or in addition to the mechanical extension stop 110, a control valve 59 can be arranged in a hydraulic line 58 leading from an extension chamber to a flexion chamber, which control valve 59 is driven by motor, such that the control motor or the control device forms the adjustment device 100, which is coupled to a controller 90. Depending on one or more measured values, for example a measured joint angle and/or a transmitted moment or interaction force, which are detected for example via a sensor 80 or several sensors 80, the hydraulic valve 59 is opened or closed via the controller 90. For example, if the extension stop is intended to be at a joint angle of 170°, the hydraulic valve 59 is closed upon attainment of a corresponding angle or corresponding orientation of the upper part 10 relative to the lower part 20 or of the first force-transmitting interface 51 relative to the second force-transmitting interface 52. A further displacement of the piston 57 inside the cylinder in the hydraulic actuator 50 is prevented, such that an extension stop is effectively formed. In addition to an embodiment of the sensor 80 as an angle sensor, it can also be configured as a force or moment sensor or as a sensor for detecting the spatial orientation of an upper part or lower part, or any desired combination of these sensors. To detect the spatial orientation, a so-called inertial angle sensor is provided, which can be arranged on the upper part or the lower part. It is also possible, with two inertial angle sensors, to determine the relative position of the upper part to the lower part and to send a corresponding control signal from the controller 90 to the adjustment device 110, so as to open or close the valve 59.

Both the hydraulic embodiment of the extension stop 110 and the mechanical embodiment of the extension stop 110 within an actuator, and also the displacement of the fastening points 15, 25 on the upper part 10 and/or lower part or on a force-transmitting interface 51, 52 or an adapter 70, can be combined with one another, and any desired combinations of the respective adjustment devices and adjustment mechanisms are possible.

Figure 13:
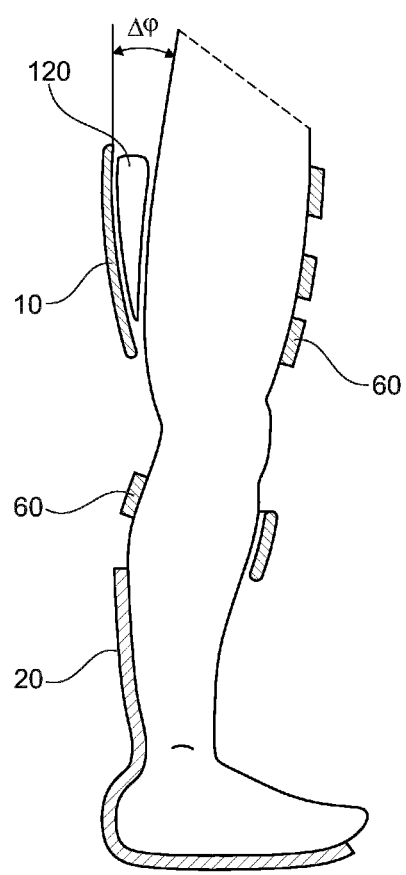
FIG. 13 shows an alternative possibility for the adjustable orientation of a lower part relative to a limb that can be secured to an upper part.

A further variant of the invention is shown in FIG. 13, in which the orthopedic device is likewise designed as an orthosis. The upper part 10 is designed as a thigh shell and is secured to the thigh via fastening devices 60 in the form of clasps or straps. By way of a joint device (not shown), the lower part 20 is secured to a foot support, and a shin support is connected via a fastening device 60 to the lower leg. To change the orientation of the lower part 20 relative to the thigh, as the limb securable to the upper part 10, a support 120 in the form of a wedge cushion or a padding is arranged on the upper part 10 at the rear aspect of the thigh. The posterior support of the thigh on the upper part 10 is adjustable by the support 120. By changing the support 120, for example by replacing the support 120 with a narrower support 120, the position of the upper limb relative to the lower part 20 is changed. The change of the angle ? between the upper part 10 and the limb can be effected either by exchanging the support 120 or by inflating a padding or by pumping a fluid in a hollow support 120. It is likewise possible to arrange a support 120 on the anterior aspect of the limb, if appropriate connected to a posterior support 120, such that, by pumping fluid from the posterior support 120 to an anterior support 120, the orientation of the thigh relative to the lower part 20 can be changed and, consequently, the extension stop can be changed. Alternatively or in addition, similar adjustments or modifications can also be made in the region of the lower leg.

In addition to a displacement of the fastening points 15, 25 as such, it is possible to alter the length of the actuator housing 55, for example by the latter being designed to be variable in length via a screw sleeve, similar to a change of length of the piston rod 56 as described with reference to FIG. 11.

By means of an orthopedic device 1 as has been described above with reference to the figures, it is possible to change the effective range of movement of the upper part 10 relative to the lower part 20 about the joint axis 40. The range of movement of the actuator 50, which can be designed to be purely passive or can also be designed as a drive, is influenced, for example, by adjustment of a mechanical extension stop, by displacement of the position of the actuator, by adjustment of fastening points 15, 25 relative to each other or to the joint axis, or by opening or closing hydraulic valves or hydraulic stops. Regardless of the way in which the extension stop is formed, the change of the extension stop can be effected for example on the basis of the joint angle and of the measured moment about the joint axis 40. By way of the measured moment and the measured angle, it is possible to detect whether the joint device 30 reaches the predefined joint angle with the predefined force. In an embodiment of the orthopedic device as an orthosis, it is by this means possible, for example, to determine how great is the muscle activity of the treated limb or of the treated body part. For example, it can be determined whether sufficient extension is applied by the thigh extensor muscles in order to move the lower part to the extension stop. The reaching of the extension stop can be used as a further control signal. With the orthopedic device described, it is possible to adapt the orthopedic device to temporal changes of the demands on the orthopedic device, for example to detect changed anatomical and physiological conditions and to adjust an extension stop if, in the course of use of the orthopedic device, a flexion contracture subsides, or if it is detected that, over a certain period of time stored in the controller, the extension stop is not reached despite the movement patterns being otherwise unchanged. This can point to damage having occurred, to fatigue having set in, or to other problems that have to be responded to during the use of the orthopedic device and that can indeed be responded to using the orthopedic device described. The change of the range of movement, in particular of the extension stop and therefore of the position of the lower part relative to the upper part, can take place automatically if defined criteria are met or are not met. An orthopedic device is thus obtained that adapts autonomously.

The sensor data are not limited to angle data or spatial position data and instead can also include forces or moments. It is possible for several sensors to be assigned to the orthopedic device. It is likewise possible that physiological data, for example electromyography sensor signals, are detected and are used to control the orthopedic device for adjusting the extension stop or the orientation of a limb relative to a lower part. By means of the predefined control data, it is possible to adjust the extension stop auto-adaptively, without a patient or an orthopedic technician having to carry out an adjustment. The auto-adaptive adjustment is effected via the adjustment device, which is driven and, in accordance with sensor data, adjusts the orthopedic device and the respective desired extension angle.

We claim:

1. An orthopedic device comprising:
  an upper part;
  a lower part connected to the upper part by at least one joint device so as to be pivotable about a joint axis;
  at least one fastening device with which the orthopedic device is securable to a limb;
  an actuator, which is secured to the upper part and the lower part at fastening points, the actuator operable to pivot the upper part relative to the lower part to adjust an orientation of the lower part relative to the limb, wherein at least one of the fastening points is mounted displaceably on the upper part or lower part or on a force-transmitting interface such that a position of the at least one fastening point on the upper part, the lower part, or the force-transmitting interface that the at least one fastening point is attached to is changed.

2. The orthopedic device as claimed in claim 1, further comprising at least one of an adjustable extension stop and a flexion stop arranged or formed on the orthopedic device, or an exchangeable or adjustable support for the limb arranged on the orthopedic device.

3. The orthopedic device as claimed in claim 2, wherein the adjustable extension stop is at least one of formed on or in the actuator, on or in a force-transmitting interface between the actuator and at least one of the upper part and lower part, or on or in the at least one joint device.

4. The orthopedic device as claimed in claim 1, wherein a distance of at least one of the fastening points from the joint axis is adjustable.

5. The orthopedic device as claimed in claim 1, wherein at least one of the fastening points is mounted to and adjustable by a motor, on the upper part or lower part or on a force-transmitting interface.

6. The orthopedic device as claimed in claim 1, wherein at least one of the fastening points is arranged or formed on an adapter on which several actuator fastening devices for the actuator are arranged.

7. The orthopedic device as claimed in claim 1, wherein at least one of the upper part, the lower part, a force-transmitting interface, and the actuator are variable in length.

8. The orthopedic device as claimed in claim 7, wherein the actuator has at least one of a housing of variable length and a piston rod of variable length.

9. The orthopedic device as claimed in claim 1, wherein at least one of the upper part, the lower part, and a force-transmitting interface have a multi-part design such that at least one of the upper part, the lower part, and the force-transmitting interface comprises a first part and a second part, the joint device is formed on the first part and at least one of the fastening points is arranged on the second part.

10. The orthopedic device as claimed in claim 1, further comprising at least one sensor for detecting at least one of a force transmitted between the upper part and the lower part and at least one of a transmitted moment, a joint angle, a spatial position of at least one of the upper part and the lower part, and biometric signals of a user.

11. The orthopedic device as claimed in claim 1, wherein the actuator is designed as a hydraulic actuator.

12. The orthopedic device as claimed in claim 11, wherein an extension stop is realized by at least one of closing a valve and blocking a hydraulic line.

13. The orthopedic device as claimed in claim 1, wherein the orthopedic device is designed as a controllable device and is provided with at least one sensor, which is coupled to a controller which activates or deactivates an adjustment device for adjusting an extension stop that limits a maximum joint angle, wherein the extension stop, in accordance with sensor data, is moved from a starting position, in which the upper part is located in a position of flexion relative to the lower part, to an end position, in which the upper part is located, relative to the lower part, in a position different than the starting position.

14. The orthopedic device as claimed in claim 13, wherein the controller is configured to detect the sensor data over a period of time and to compare them to a threshold value, wherein an adjustment of the extension stop takes place only when the threshold value is reached over a defined period of time.

15. The orthopedic device as claimed in claim 13, wherein the maximum joint angle is adjustable, and, in accordance with a measured joint angle, the extension stop is adjustable as far as the maximum joint angle.

16. The orthopedic device as claimed in claim 13, wherein the controller is configured such that, when the extension stop is reached, a moment effective about the joint axis or a force effective between the upper part and the lower part is measured, and, if a threshold value is exceeded, the extension stop is moved in a direction of its end position, and, if the threshold value is not reached, the extension stop is moved in an opposite direction.

17. The orthopedic device as claimed in claim 13, wherein the controller is configured to receive resistance values of the actuator during the pivoting movement and to correlate the resistance values with sensor values concerning a joint angle and at least one of forces and moments prevailing between the upper part and the lower part, and, if a force and moment profile deviates from a resistance profile, to perform an adjustment of the extension stop.

18. The orthopedic device as claimed in claim 13, wherein the extension stop is adjustable auto-adaptively.

* * * * *